United States Patent [19]
McGahan

[11] Patent Number: 6,095,981
[45] Date of Patent: Aug. 1, 2000

[54] APPARATUS FOR ATTACHMENT OF NEEDLE OR CATHETER TO ENDOLUMINAL ULTRASOUND PROBE

[75] Inventor: John P. McGahan, Sacramento, Calif.

[73] Assignee: The Regents of The University of California, Oakland, Calif.

[21] Appl. No.: 09/108,877

[22] Filed: Jul. 1, 1998

[51] Int. Cl.⁷ .................................................. A61B 8/14
[52] U.S. Cl. ...................... 600/461; 600/462; 600/466
[58] Field of Search ................. 600/459, 461, 600/462, 463, 464, 466, 471; 604/116, 164, 195, 464; 606/130, 139

[56] References Cited

U.S. PATENT DOCUMENTS

| | | |
|---|---|---|
| 4,108,165 | 8/1978 | Kopp et al. . |
| 4,363,326 | 12/1982 | Kopel . |
| 4,402,324 | 9/1983 | Lindgren et al. . |
| 4,489,730 | 12/1984 | Jingu . |
| 4,542,747 | 9/1985 | Zurinski et al. . |
| 4,635,644 | 1/1987 | Yagata . |
| 4,742,829 | 5/1988 | Law et al. ................................. 600/461 |
| 5,052,396 | 10/1991 | Wedel et al. ............................. 600/461 |
| 5,343,865 | 9/1994 | Gardineer et al. . |
| 5,469,853 | 11/1995 | Law et al. ................................. 600/462 |
| 5,924,992 | 7/1999 | Park et al. ............................... 600/461 |

FOREIGN PATENT DOCUMENTS

WO 84/03034  8/1984  WIPO .

*Primary Examiner*—Marvin M. Lateef
*Assistant Examiner*—Ali M. Imam
*Attorney, Agent, or Firm*—John P. O'Banion

[57] ABSTRACT

A needle guidance attachment device for an endoluminal ultrasound probe that allows removal of the probe while the needle is in position in the tissue. The device includes an elongated needle carrier having a longitudinal slot with a transverse opening. The carrier includes a pair of retaining bands adapted to fit around a cylindrical-shaped ultrasound transducer and to orient the needle carrier along the longitudinal axis of the probe. An elongated cover is slidably coupled to the carrier in a longitudinal orientation such that at least a portion of the slot is covered in a first, closed position and uncovered in a second, opened position. The cover moves between its open and closed position axially about the longitudinal axis of the needle carrier.

14 Claims, 7 Drawing Sheets

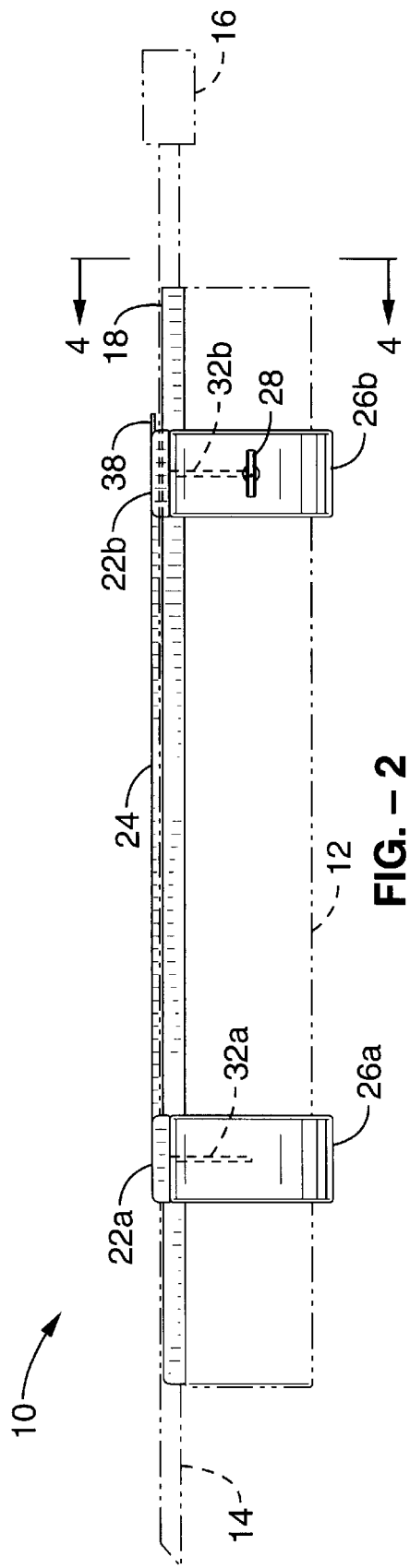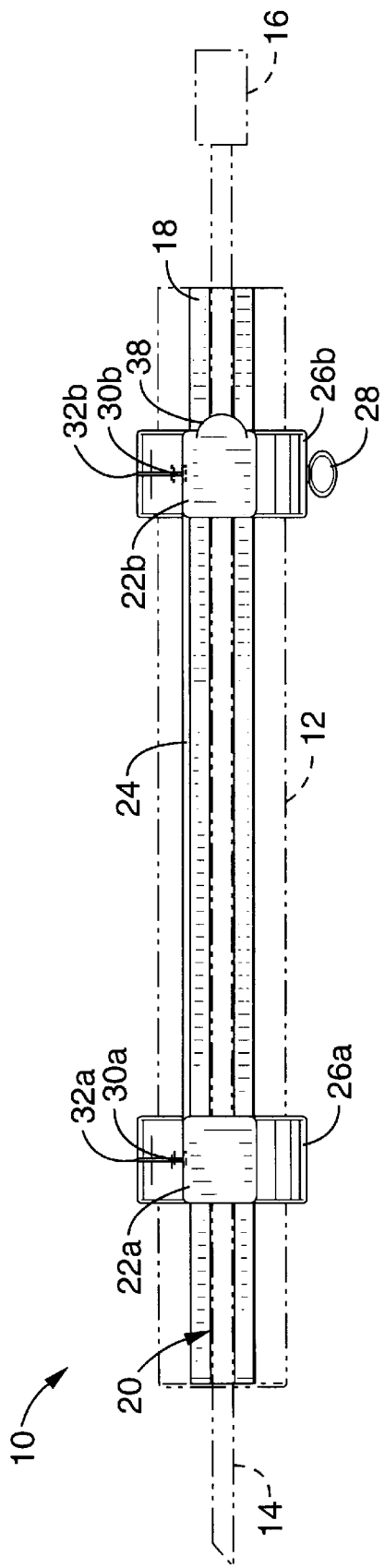

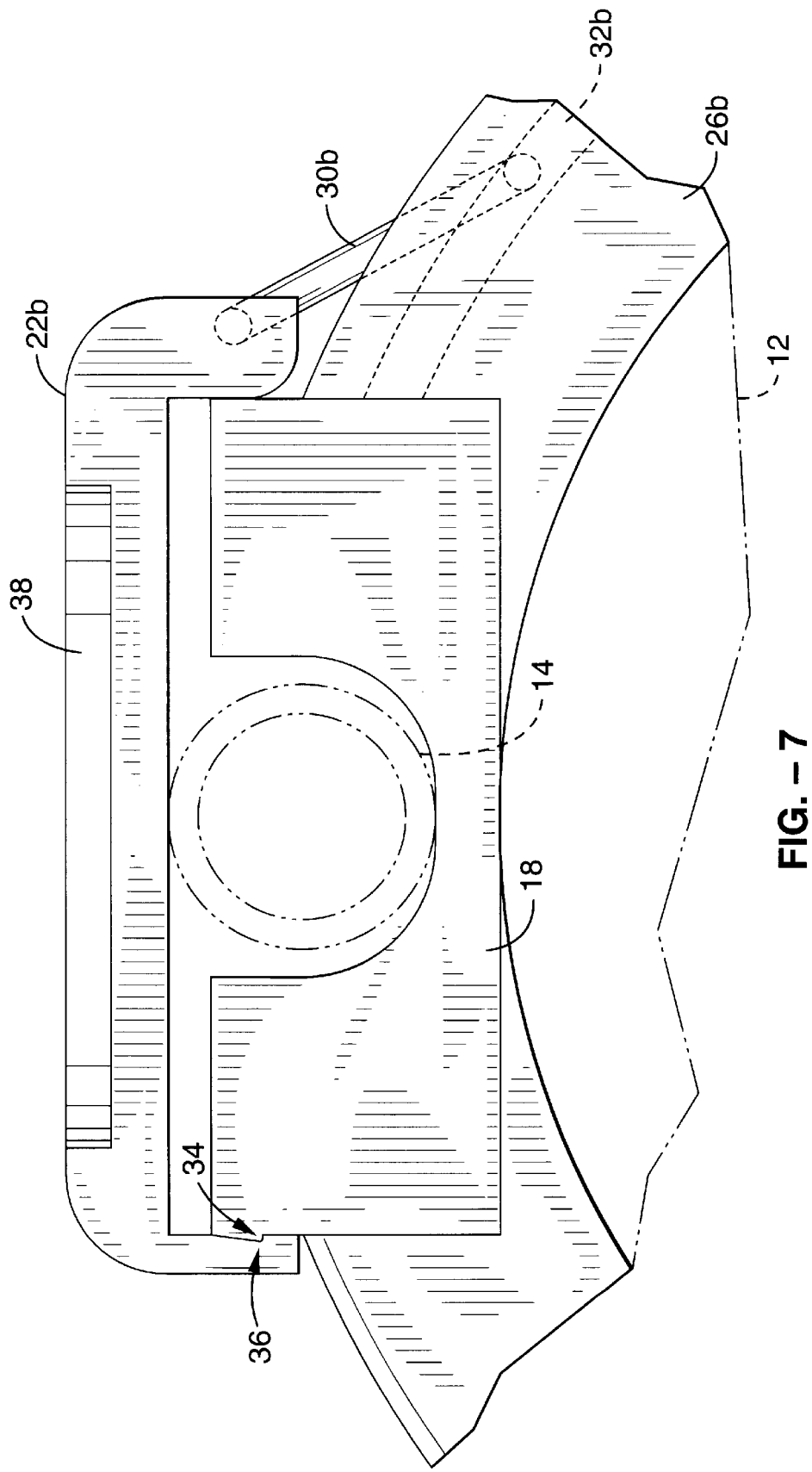

ID="6,095,981"

APPARATUS FOR ATTACHMENT OF NEEDLE OR CATHETER TO ENDOLUMINAL ULTRASOUND PROBE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to needle guidance devices, and more particularly to a needle carrier for attachment to an ultrasound transducer.

2. Description of the Background Art

Ultrasound imaging is a well known tool used by the medical profession for locating an area of tissue in the body. For example, ultrasound imaging is used in various procedures, such as biopsy or aspiration of fluid collection, to locate a specific tissue site and to guide a needle to that site through a body cavity. Ultrasound probes that are specially designed to fit into body cavities such as the vagina or rectum are well known, and a number of needle attachments are available for such probes. Generally, these attachments fit over the ultrasound probe and hold the needle in place for ultrasound guidance into tissue such as the ovary or prostate for aspiration or biopsy. Conventional needle holding attachments for such probes have a slot or groove which circumferentially surrounds the needle after it is placed. As a result, withdrawal of the probe from the body cavity also dictates removal of the needle due to engagement of the needle hub during withdrawal of the probe. Separation of the needle from the probe is also impeded by the confines of a body cavity into which a probe and needle is placed, as there is generally a lack of sufficient range of motion for otherwise disengaging the needle from the transducer.

There is currently no needle holding attachment for an ultrasound probe for body cavities that allows for the needle to be removed from its groove or slot and left in place after the probe has been removed from the body cavity. This is a significant drawback in that the probe can interfere with the biopsy or aspiration procedure once the needle is placed. Therefore, there is a need for a device which positions the needle on the periphery of the transducer so as to facilitate removal of the transducer from the needle with a small amount of lateral movement. The present inventions satisfies that need, as well as others, and overcomes the deficiencies inherent in conventional needle carrier devices.

BRIEF SUMMARY OF THE INVENTION

The present invention addresses the deficiencies of conventional needle attachment devices used in conjunction with ultrasonic imaging in body cavities by positioning the needle (including a catheter) in a slot on the periphery of the transducer so as to facilitate removal of the transducer from the needle with a small amount of lateral movement. By way of example, and not of limitation, the invention generally comprises a needle guidance attachment device for an endoluminal ultrasound probe that allows removal of the probe while the needle is in position in the tissue.

In accordance with an aspect of the invention, the device includes an elongated needle carrier having a longitudinal slot for receiving a needle.

In accordance with another aspect of the invention, the needle carrier includes a pair of retaining bands adapted to fit around a cylindrical-shaped ultrasound probe and to orient the needle carrier along the longitudinal axis of the probe.

In accordance with still another aspect of the invention, a cover is provided that is moveable between first, closed position where at least a portion of the slot is covered, and a second, opened position where the slot is exposed. The cover moves between its open and closed position axially about the longitudinal axis of the needle carrier. The cover slides or rotates on a slotted track so that it can be opened for needle removal.

An object of the invention is to provide a needle attachment apparatus that allows for removal of the ultrasound probe after the needle is placed.

Another object of the invention is provide a needle attachment apparatus that allows for removal of the ultrasound probe without removing the needle.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 2 is side elevation view of the apparatus shown in FIG. 1.

FIG. 3 is a top plan view of the apparatus shown in FIG. 1.

FIG. 7 is a fragmentary enlarged view corresponding to FIG. 4.

DETAILED DESCRIPTION OF THE INVENTION

Referring more specifically to the drawings, for illustrative purposes the present invention is embodied in the apparatus generally shown in FIG. 1 through FIG. 9. It will be appreciated that the apparatus may vary as to configuration and as to details of the parts without departing from the basic concepts as disclosed herein.

Figure 1:
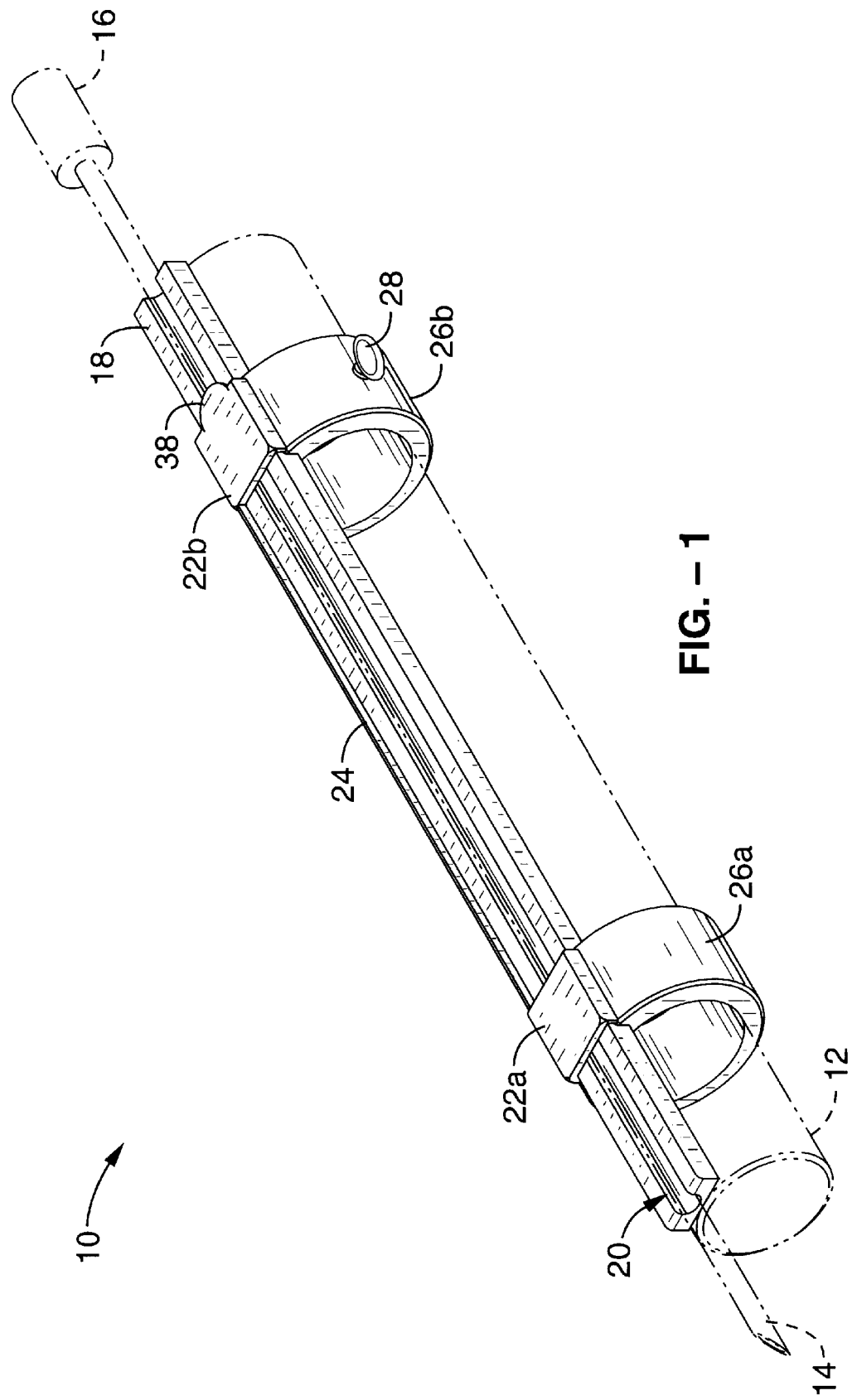
FIG. 1 is a perspective view of a needle attachment apparatus in accordance with the present invention.

Referring first to FIG. 1, a needle carrier apparatus 10 in accordance with the present invention is shown coupled to a conventional ultrasound transducer 12 and is further shown carrying a conventional needle 14 having a hub 16. Those skilled in the art will appreciate that hub 16 prevents conventional needle carrier/transducer assemblies from being removed from a body cavity without engaging hub 16 and removing needle 14 at the same time. Additionally, the term "needle" as used herein encompasses needles, catheters and the like.

As shown in FIG. 1 through FIG. 3, the invention includes a needle carrier 18 for positioning needle 14 in a longitudinal orientation in relation to transducer 12. Needle carrier 18 includes a longitudinal slot 20 for receiving needle 14. Slot 20 is preferably sized to retain needle 14 without lateral play so as to maintain placement accuracy without frictional engagement that would impede removal of the needle from the slot.

A pair of spaced-apart distal 22a and proximal 22b covers, which are coupled to needle carrier 18 and joined by an elongated and preferably rigid stem 24, extend over needle 14 and slot 20 to hold needle 14 in place within slot 20. It will be appreciated that any number of covers, including a single cover, could be used as well without departing from the scope of the invention. It will also be appreciated that it is unnecessary for the covers to extend over the entire length of the slot.

Needle carrier 18 is preferably coupled to transducer 12 by coupling means preferably comprising a pair of distal 26a and proximal 26b ring shaped fasteners which are positioned in longitudinal alignment with covers 22a, 22b, respectively. It will be appreciated that any number of rings, including a single ring, could be used as well without departing from the scope of the invention. Transducer 12 fits within rings 26a, 26b, and the longitudinal position of the apparatus in relation to transducer 12 is held fixed by locking means 28, which is preferably a screw type fastener which extends through threads in ring 26b and engages transducer 12 when tightened. While only one fastener is shown, a second fastener could be included on ring 26a if desired. Additionally, the locking means could alternatively comprise a set screw or any other type of fastener, although it is preferred that the fastener by of a type that allows the ring to be disconnected from the transducer. It will also be appreciated that other detachable coupling means, such as slotted joints (e.g., dovetail or dado-like joints), adjustable circumference bands or the like, could be employed to fasten needle carrier 18 to transducer 12 instead of using rings 26a, 26b.

Figure 4:
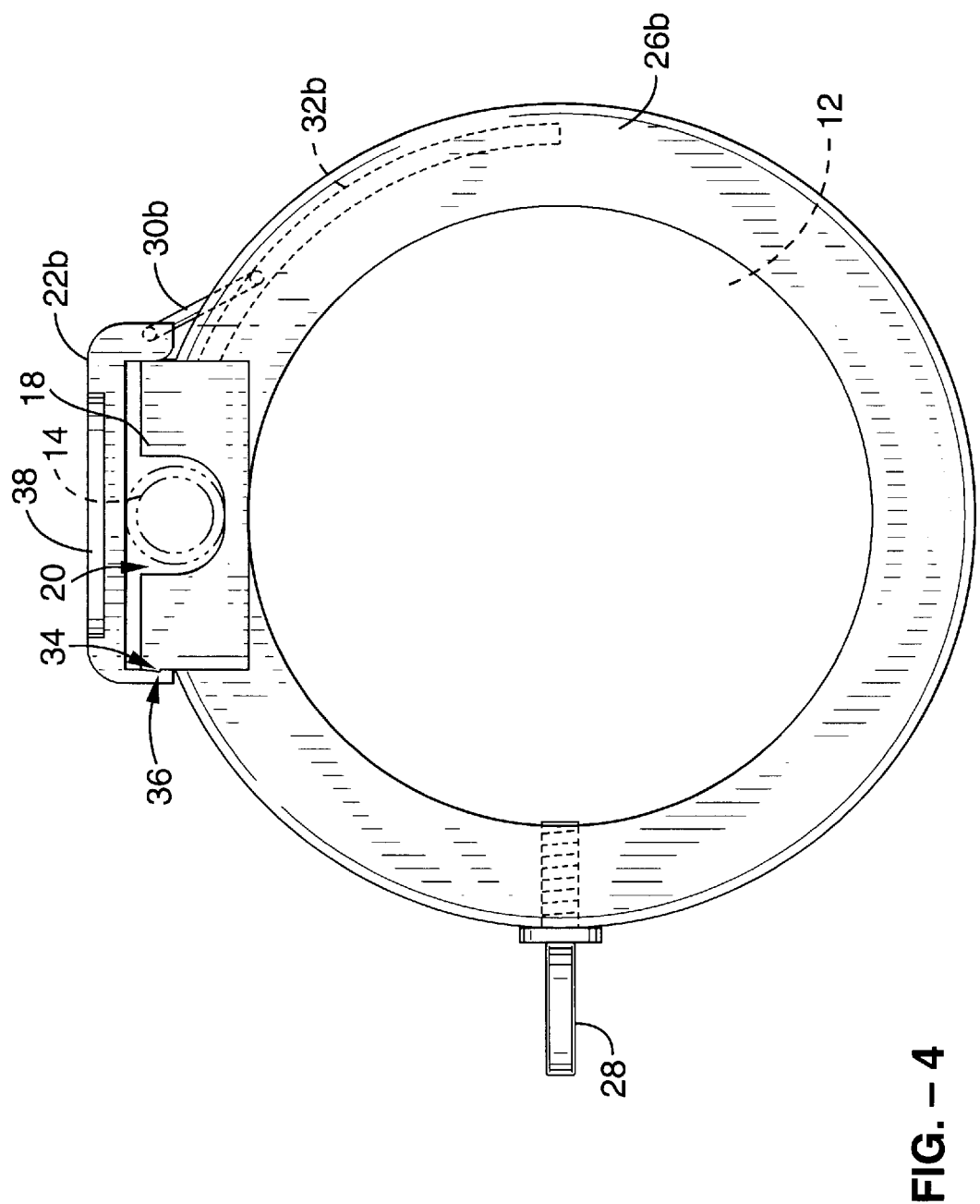
FIG. 4 is a cross-sectional view of the apparatus shown in FIG. 2 taken through line 4—4 showing the cover in a closed position.
Figure 5:
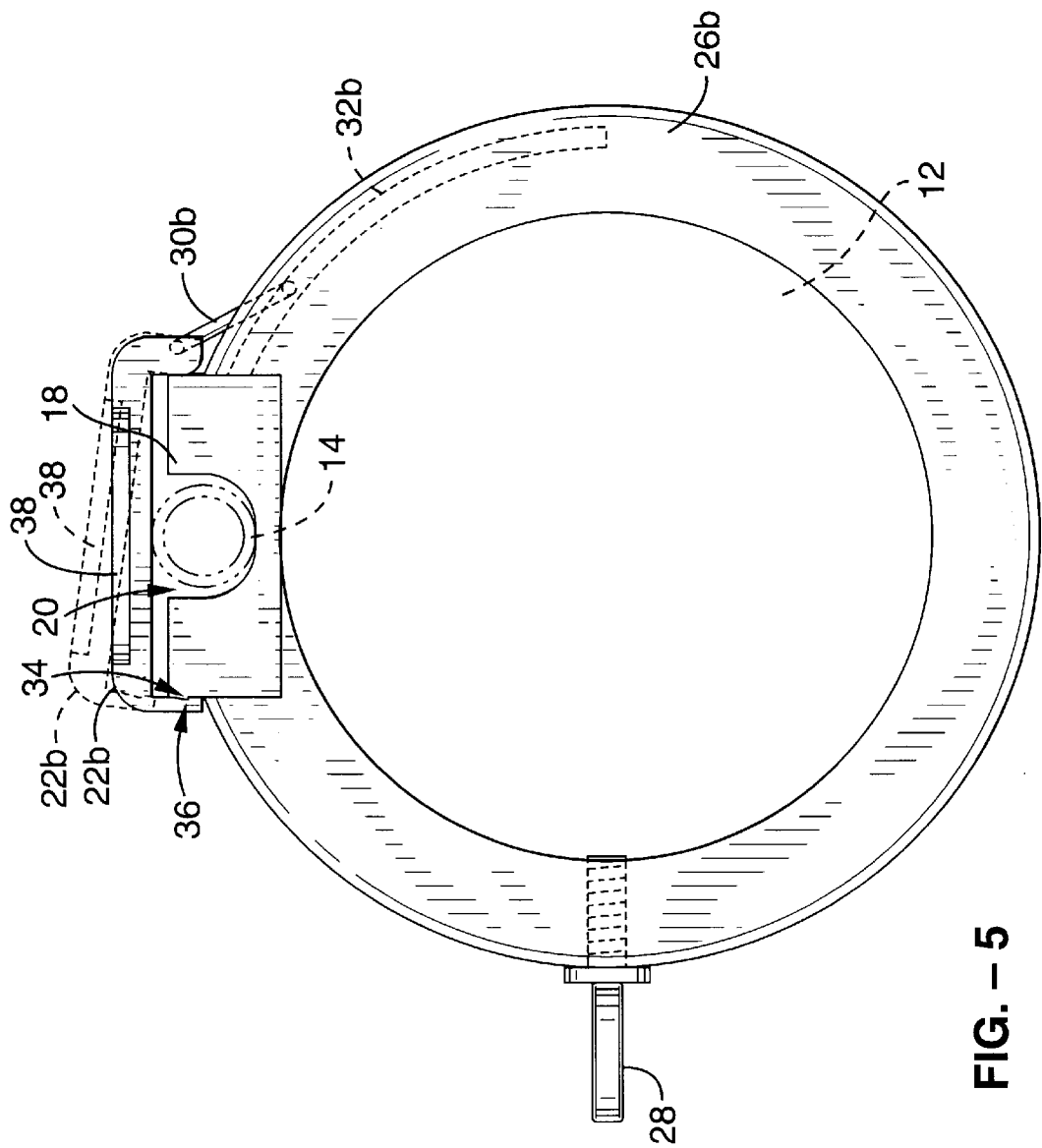
FIG. 5 is a cross-sectional view of the apparatus corresponding to FIG. 4 diagrammatically showing movement of the cover toward an open position.
Figure 6:
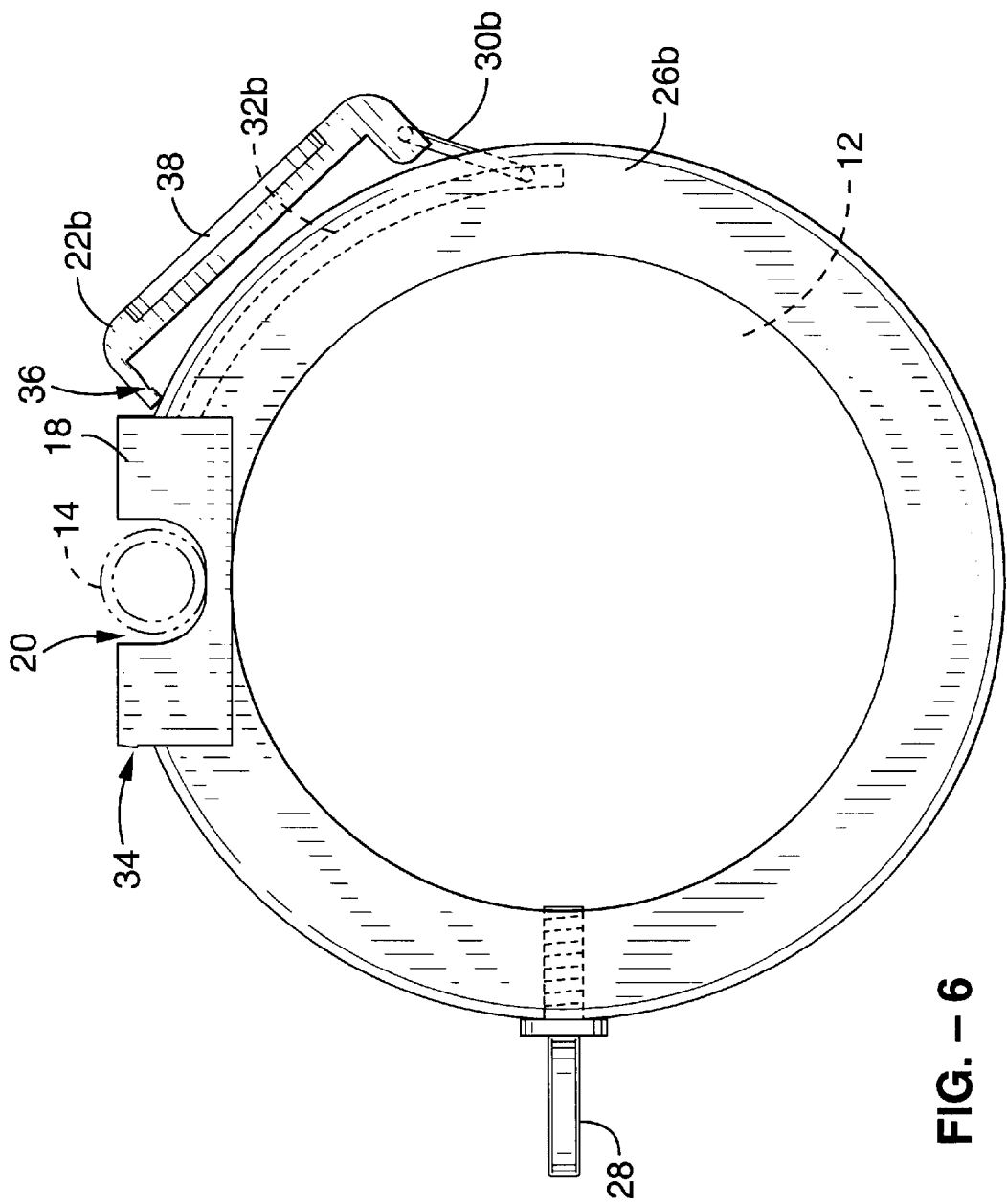
FIG. 6 is a cross-sectional view of the apparatus corresponding to FIG. 4 showing the cover in an open position.
Figure 9:
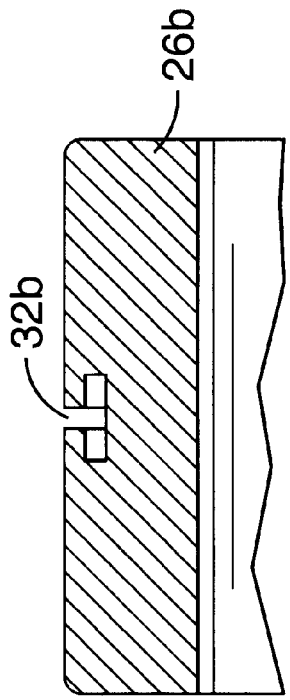
FIG. 9 is a cross-sectional view of the track portion of the apparatus shown in FIG. 8 taken through line 9—9.
Figure 8:
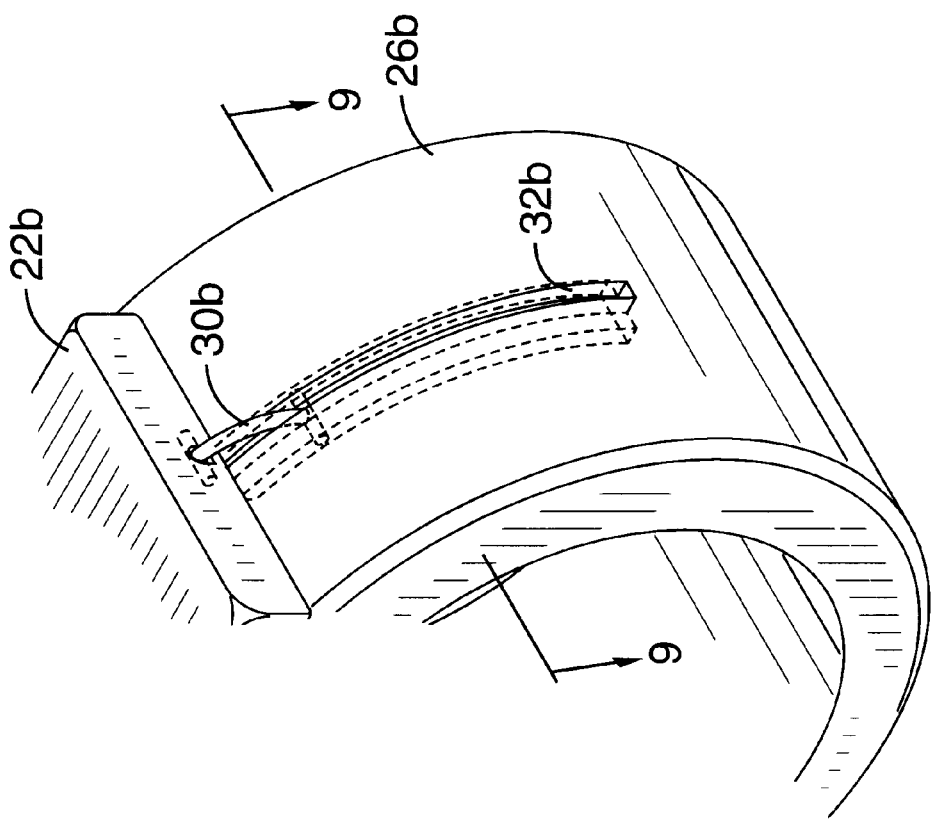
FIG. 8 is a fragmentary enlarged view of a portion of the apparatus of FIG. 1 showing the hinge and track portion of the apparatus.

Referring now to FIG. 4 through FIG. 6, covers 22a, 22b are preferably pivotally and/or slidably attached to rings 26a, 26b, respectively, so that the covers can be moved between a first, closed position over slot 20 where needle 14 is held within slot 20 as shown in FIG. 4, and a second, open position, where slot 20 is exposed and needle 14 can be removed as show in FIG. 6. To facilitate this operation, the apparatus preferably includes hinge means for pivotally coupling covers 22a, 22b to needle carrier 14, as well as track means for slidably coupling covers 22a, 22b to rings 26a, 26b. The hinge means preferably comprises double T-bar type hinges 30a, 30b, the details of which can be seen by referring also to FIG. 7 through FIG. 9. One end of each of hinges 30a, 30b is preferably pivotally coupled to cover 22a, 22b, respectively, and the other end is preferably pivotally and slidably coupled to rings 26a, 26b by means of slots 32a, 32b, respectively, which function as a track means along which the covers can move between the open and closed position, as well as an additional pivot point for hinges 30a, 30b. While the preferred embodiment is shown, it will be appreciated that the hinges could be fixedly coupled to the covers, although this would limit articulation of the covers and potentially make retraction of the covers more difficult. Other hinge mechanisms could be used as well. However, to enable use of the invention in tight body cavities, such as in the vagina or rectum, the radial travel of the covers needs to be minimized and circumferential movement around the transducer enhanced. This is accomplished using the slide and pivot hinge mechanism previously described.

Referring now to FIG. 1, FIG. 3, FIG. 6 and FIG. 7, at least one cover includes latching means to hold the cover assembly (22a, 22b, 24) in its closed position during use of the apparatus. Here, cover 22b and needle carrier 18 are shown with mating snap-type tongue 34 and groove 36 latch members which form the latching means. By making cover 22b resilient, it can be snapped into place upon closure. This will result in needle 14 being held firmly in place. To facilitate opening cover 22b, a proximal tab 38 for applying a radial force to open cover 22b. Tab 38 is preferably aligned with the longitudinal axis of needle carrier 18 as shown due to the limited space in a body cavity for accessing the tab.

Referring again to FIG. 4 through FIG. 6, The needle would be guided ultrasonically and placed in the tissue when the covers are in the closed position as shown in FIG. 4. After the needle punctures the tissue, the cover assembly is moved to the open position as shown in FIG. 6, thus allowing the needle to be removed from the slot. The ultrasound probe can then be removed, leaving the needle in position.

While the invention is used in combination with an ultrasound probe and a needle, those elements do not form a part of the preferred embodiment of the invention and are presented for clarifying the context of the invention. It is contemplated, however, that the invention could optionally be provided as an integral part of an ultrasound transducer and permanently coupled thereto. It will also be appreciated that the invention could be used with ultrasound transducers and needles of varying structural configurations.

Accordingly, it will be seen that this invention provides for attachment of a biopsy or aspiration needle to an ultrasound probe in a manner wherein the probe can be removed once the needle is placed in the tissue and the needle left in place. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A needle attachment apparatus for an endoluminal ultrasound probe comprising:

(a) a needle carrier, said needle carrier including a longitudinal slot; and (b) a cover coupled to said needle carrier, said cover moveable between a first, closed position over said slot and a second, open position, wherein a needle placed in said needle carrier is retained for insertion though a body cavity and into tissue when said cover is in said first, closed position, and wherein said needle carrier can be laterally detached from said needle and removed from said body cavity when said cover is in said second, open position, without removal of said needle from said tissue or said body cavity.

2. An apparatus as recited in claim 1, further comprising a receptacle for configured to couple said apparatus to an ultrasound probe.

3. An apparatus as recited in claim 2, wherein said receptacle comprises an annular ring coupled to said needle carrier and further comprising a locking mechanism configured to lock said annular ring to an ultrasound probe.

4. An apparatus as recited in claim 2, wherein said cover is pivotally coupled to said annular ring.

5. An apparatus as recited in claim 2, wherein said cover is slidably coupled to said annular ring.

6. An apparatus as recited in claim 5, further comprising a slot in said annular ring and a hinge pivotally coupling said cover to said needle carrier, wherein said slot receives said hinge, and wherein said hinge slides in said slot.

7. An apparatus as recited in claim 1, wherein said cover and said needle carrier include a cooperating latch mechanism.

8. An apparatus for detachably coupling a needle to an ultrasound transducer, comprising:

(a) an elongated needle carrier, said needle carrier including a longitudinal slot;

(b) a receptacle configured to couple said apparatus to an ultrasound transducer in a fixed position; and (c) a cover coupled to said annular ring, said cover moveable between a first, closed position over said slot and a second, open position away from said slot, wherein a needle placed in said needle carrier is retained for insertion though a body cavity and into tissue when said cover is in said first, closed position, and wherein said needle carrier can be laterally detached from said needle and removed from said body cavity when said cover is in said second, open position, without removal of said needle from said tissue or said body cavity.

9. An apparatus as recited in claim 8, wherein said cover and said needle carrier include a cooperating latch mechanism.

10. An apparatus as recited in claim 8, wherein said receptacle comprises an annular ring and wherein said cover is pivotally coupled to annular ring.

11. An apparatus as recited in claim 10, wherein said cover is slidably coupled to said annular ring.

12. An apparatus as recited in claim 11, further comprising a slot in said annular ring and a hinge pivotally coupling said cover to said needle carrier, wherein said slot receives said hinge, and wherein said hinge slides in said slot.

13. A needle attachment apparatus for an endoluminal ultrasound guidance probe, comprising:

(a) an elongated needle carrier, said needle carrier including a longitudinal slot;

(b) an annular ring coupled to said needle carrier and configured for coupling said needle carrier to an ultrasound transducer in a fixed position;

(c) a cover;

(d) a cooperating latch mechanism associated with said cover and said needle carrier; and (e) a hinge pivotally coupling said cover to said annular ring wherein said cover extends over at least a portion of said slot in a first, closed position and exposes said slot in a second open position, wherein a needle placed in said needle carrier is retained for insertion though a body cavity and into tissue when said cover is in said first, closed position, and wherein said needle carrier can be laterally detached from said needle and removed from said body cavity when said cover is in said second, open position, without removal of said needle from said tissue or said body cavity.

14. An apparatus as recited in claim 13, further comprising a slot in said annular ring for receiving said hinge wherein said hinge slides in said slot.

* * * * *